(12) United States Patent
Stahl et al.

(10) Patent No.: US 8,729,123 B2
(45) Date of Patent: May 20, 2014

(54) NUTRITION CONTAINING FAT BLEND

(75) Inventors: Bernd Stahl, Rosbach (DE); Gunther Boehm, Echzell (DE); Christopher Beermann, Neu-Anspach (DE); Johan Garssen, Nieuwegein (NL)

(73) Assignee: N.V. Nutricia, Zoetermeer H.M. (NL)

( * ) Notice: Subject to any disclaimer, the term of this patent is extended or adjusted under 35 U.S.C. 154(b) by 246 days.

(21) Appl. No.: 13/251,399

(22) Filed: Oct. 3, 2011

(65) Prior Publication Data

US 2012/0027885 A1    Feb. 2, 2012

Related U.S. Application Data

(62) Division of application No. 11/666,990, filed as application No. PCT/EP2005/012122 on Nov. 11, 2005, now Pat. No. 8,053,471.

(30) Foreign Application Priority Data

Nov. 11, 2004   (EP) ..................................... 04026825

(51) Int. Cl.
*A61K 31/22* (2006.01)
*A61K 31/20* (2006.01)

(52) U.S. Cl.
USPC ............ 514/546; 514/558; 514/559; 514/560

(58) Field of Classification Search
USPC ................. 514/546, 558, 559, 560
See application file for complete search history.

(56) References Cited

U.S. PATENT DOCUMENTS 5,886,037 A    3/1999   Klor et al.

FOREIGN PATENT DOCUMENTS

| EP | 0484 266 A | 5/1992 |
|---|---|---|
| EP | 0 775 449 A1 | 5/1997 |
| EP | 0 823 475 | 2/1998 |
| EP | 0823475 A1 | 2/1998 |
| EP | 1809125 B1 | 2/2010 |
| WO | 9836745 A2 | 8/1998 |
| WO | WO 98/36745 A | 8/1998 |
| WO | WO 00/20603 A1 | 4/2000 |
| WO | WO 00/40705 A2 | 7/2000 |
| WO | WO 01/78530 A2 | 10/2001 |
| WO | WO 02/009540 A1 | 11/2002 |
| WO | WO 2004/052115 A1 | 6/2004 |

OTHER PUBLICATIONS

Notice of Opposition to EP 1 809 125 filed on Dec. 28, 2010, in corresponding European Patent Application No. 05813382.8.
Product Label: Frisomel Advance 2—follow on milk, D1. 2010.
Product Label: Frisolac Advance-Infant milk, D2. 2010.
Product Label: Friso 1 Infant formula, D3. 2010.
Product packaging: Frisolac Advance Infant Milk Can, D4. 2010.
Table: Friso brand products, fatty acid composition thereof, D5. 2010.
Pestka, James J. et al., "Dietary Fish Oil Suppresses Experimental Immuniglobulin a Nephropathy in Mice," Nutritional Immunology 132 (2002) 261-269, D6.
Koletzko, Berthold et al., "Physiological aspects of human milk lipids," Early Human Development 65 Suppl. (2001) S3-S18, D7.
Ghebremeskel, Kebreab et al., "Type 1 Diabetes Compromises Plasma Arachidonic and Docosahexaenoic Acids in Newborn Babies," Lipids 2004, 39(4), 335-342, D8.
Hansen, Harald S., "New Biological and Clinical Roles for the n-6 and n-3 Fatty Acids," Nutrition Reviewed, 52(5) 1994, 1620167, D9.
Wijendran, Vaduki et al., "Fetal Erythrocyte Phospholipid Polyunsaturated Fatty Acids are Altered in Pregnancy Complicated with Gestational Diabetes Mellitus," Lipids 35(8) 2000, 927-931, D10.
Andersen, Steen et al., "Microencapsulated Marine Omega-3 Fatty Acids for Use in the Food Industry," Food Tech Europe Dec. 1994/Jan. 1995, D11.
Carlson, Susan E. et al., "Effect of Fish Oil Supplementation on the n-3 Fatty Acid Content of Red Blood Cell Membranes in Pre-term Infants," Pediatric Research, 21(5), 1987, D12.

*Primary Examiner* — Kevin E Weddington
(74) *Attorney, Agent, or Firm* — Bacon & Thomas, PLLC

(57) ABSTRACT

The invention relates to the use of long chain polyunsaturated fatty acids for the manufacture of a nutritional composition for feeding infants of a mother who suffered from a metabolic disorder during pregnancy and to a corresponding composition. Said composition comprises a n-3 polyunsaturated fatty acid fraction containing at least 0.1 wt % docosahexaenoic acid (DHA) based on total weight of the lipid, at least 0.01 wt % n-3 docosapentaenoic acid (DPAn-3) based on total weight of the lipid, and at least 0.01 wt. % eicosapentaenoic acid (EPA) based on total weight of the lipid, wherein the sum of DHA, DPAn-3 and EPA is below 1 wt. % of total lipid.

6 Claims, No Drawings

NUTRITION CONTAINING FAT BLEND

This application is a divisional application of pending U.S. patent application Ser. No. 11/666,990, filed on Sep. 20, 2007, which is the U.S. national phase of International Patent Application No. PCT/EP05/12122, filed on Nov. 11, 2005, which claims priority to European Patent Application No. EP04026825.2, filed on Nov. 11, 2004, the entire disclosures of which are incorporated herein by reference.

FIELD OF THE INVENTION

The present invention relates to the use of a long chain polyunsaturated fatty acid composition for feeding an infant of a mother who suffered from a metabolic disorder during pregnancy and a nutritional composition with polyunsaturated fatty acids suitable for such use.

BACKGROUND OF THE INVENTION

The polyunsaturated fatty acid status of infants is of continuing interest in the art. Several functions have been attributed to different fatty acids. For example, docosahexaenoic acid (DHA) is the primary structural fatty acid component in both the gray matter of the brain and the retina of the eye and thus is essential for brain and eye function. Hence, DHA is of particular importance for the growing infant.

As a result of DHA deficiency, n-6 docosapentaenoic acid (DPA n-6) is instead incorporated in the growing brain of the infant. This is undesirable because it is difficult to reverse and may result in impaired neurological development. Additional, insufficient DHA may lead to a hindrance of healthy development.

DHA deficiency is of particular importance for infants of mothers who suffered from a disease during pregnancy. Hence, particularly for these infants, it is of crucial importance that the infant formula provides an optimal fatty acid profile in the infant.

DE 4 327 310 describes a milk composition from cows containing eicosapentaenoic acid (EPA), docosahexaenoic acid (DHA) and n-3 docosapentaenoic acid (DPA-n3), which is useful for promoting growth, intellectual function and sight function in children. The fat composition is however unsuitable for feeding to an infant because the weight ratio linoleic acid/alpha-linolenic acid (LA/ALA) is not optimal.

WO 01/78530 describes a nutritional composition containing specified amounts of docosahexaenoic acid (DHA) and arachidonic acid (AA) as well as their precursor essential fatty acids ALA and LA, for providing nutrition and for enhancing neurological development of preterm infants.

WO 2004/052115 describes glyceride compositions, methods of making the glyceride compositions, and nutritional formulations containing the glyceride compositions. The glyceride compositions contain predominantly monoglycerides and diglycerides carrying one or more long chain polyunsaturated fatty acids. Also disclosed are methods of using the glyceride compositions and nutritional formulations.

WO 98/36745 describes methods and compositions for reducing the incidence of necrotizing enterocolitis. Said compositions provide n-6 and n-3 long-chain polyunsaturated fatty acids.

The object of the present invention is to provide a nutritional composition with polyunsaturated fatty acids suitable for feeding an infant of a mother who suffered from a metabolic disorder during pregnancy.

SUMMARY OF THE INVENTION

The present inventors believe that not only DHA and AA need to be abundantly present in infant formula for optimal brain development, but also the precursors of these fatty acids are essential because an important part of the DHA and AA are locally synthesized in the brains from its precursors. Hence, the present inventors believe that addition of DHA and/or AA alone to the standard infant formulas is insufficient to provide optimal DHA incorporation in the various neurological tissues. Hence the present composition also contains, besides DHA and AA, significant amounts of precursors of DHA and AA.

For an optimal de novo synthesis, the present composition contains the precursors of DHA, including at least alpha-linolenic acid (ALA), eicosapentaenoic acid (EPA) and n-3 docosapentaenoic acid (DPA-n3). However, EPA cannot be included in the composition in to high amounts, as EPA inhibits the metabolic conversion of linolenic acid (LA) to AA, another important fatty acid. The relatively low EPA amounts are compensated for by relatively high quantities of docosapentaenoic acid (DPAn-3) in the present composition. Both precursors are essential, because they are believed to provide the precursors, which stimulate the local DHA synthesis.

Hence, in an optimal configuration, the weight EPA/DHA ratio in the present composition is between 0.05 and 1, which is similar or a little below the ratio of the average human milk;

the weight ratio long chain DHA precursor [DPAn-3+EPA] per DHA is preferably between 0.25 and 1 in order to provide sufficient DHA precursor; and the weight ratio DPA-n3/EPA of the present composition is between 0.25 and 5. Human milk generally has a weight ratio DPA-n3/EPA above about 1.

High DPAn-3 oils, which can be suitably used, include marine oils such as seal oil and DPAn-3-enriched fish oils. The present composition has a weight ratio DHA/DPAn-3 of between 2 and 25, slightly above the average content weight ratio DHA/DPA-n3 in human milk, but a major improvement over the available infant formula containing no or only trace amounts of DPA-n3.

In order to further improve the composition, ALA is added in significant amounts to further reduce insufficiency of DHA. The ratio ALA/DHA in the present composition is preferably between 5 and 25.

Furthermore, it is of great importance that arachidonic acid (AA) is included in the present composition, particularly in those compositions containing long chain precursors of docosahexaenoic acid. AA is an omega-6 fatty acid derived from linoleic acid and is found primarily in food sources such as meat, eggs and milk. AA contains twenty carbon atoms and four double bonds (20:4n-6) and is the principal omega-6 fatty acid found in the brain. Besides AA it is also of primary importance that the lipid contains significant amounts of AA precursor, i.e. gamma linolenic acid (GLA) and linoleic acid (LA). These fatty acids provide the precursor for local synthesis of AA. Because the present composition has a high GLA content, i.e. preferably between 0.05 and 0.4 wt. % GLA based on total weight of the lipid, the present composition has a low linoleic acid content, i.e. between 10 and 15 wt. % LA based on total weight of the lipid.

DETAILED DESCRIPTION OF THE PREFERRED EMBODIMENTS

The present invention provides a nutritional composition wherein the carbohydrate provides 40 to 75% of the total calories, the lipid provides 20 to 50% of the total calories and the protein provides 5 to 12.5% of the total calories, wherein the lipid contains at least one vegetable lipid source and a n-3 docosapentaenoic acid (DPAn-3) containing lipid source, said lipid contains an n-3 polyunsaturated fatty acid fraction and an n-6 polyunsaturated fatty acid fraction, wherein the n-3 polyunsaturated fatty acid fraction contains at least 0.1 wt % docosahexaenoic acid (DHA) based on total weight of the lipid; at least 0.01 wt % DPAn-3 based on total weight of the lipid; at least 0.01 wt. % eicosapentaenoic acid (EPA) based on total weight of the lipid; wherein the sum DHA, DPAn-3 and EPA is below 1 wt. % of total lipid; and between 1.9 and 3 wt. % alpha linoleic acid (ALA) based on total weight of the lipid; and the weight ratio: EPA/DHA ratio between 0.05 and 1; (DPAn-3+EPA)/DHA 0.25 and 1; DPAn-3/EPA 0.25 and 5; DHA/DPAn-3 between 2 and 25; ALA/DHA between 5 and 25, the n-6 polyunsaturated fatty acid fraction contains between 0.2 and 1 wt. % arachidonic acid (AA) based on total weight of the lipid; and between 10 and 15 wt. % linoleic acid (LA) based on total weight of the lipid; and the weight ratio LA/ALA is between 5 and 10.

The present composition, which can be considered as a nutrition containing a lipid blend, can suitably be used for feeding healthy infants and is particularly suitable for feeding an infant of a mother who suffered from a metabolic disorder during pregnancy. The n-3 polyunsaturated fatty acid fraction as described above provides significant benefits for these infants. Optimally, the composition as described above contains both the n-3 polyunsaturated fatty acid fraction and the n-6 polyunsaturated fatty acid fraction as described herein.

In a further aspect the present invention provides the use of long chain polyunsaturated fatty acids for the manufacture of a nutritional composition, which is preferably a liquid composition, for feeding infants of a mother who suffered from a metabolic disorder during pregnancy, said composition comprising a n-3 polyunsaturated fatty acid fraction containing at least 0.1 wt % docosahexaenoic acid (DHA) based on total weight of the lipid; and at least 0.01 wt % n-3 docosapentaenoic acid (DPA-n3) based on total weight of the lipid; and at least 0.01 wt. % eicosapentaenoic acid (EPA, n3) based on total weight of the lipid; and wherein the sum DHA, DPA-n3 and EPA is below 1 wt. % of total lipid. Said nutritional composition can have any form desired and/or suitable for feeding purposes and is preferably in the form of a liquid.

The present composition is particularly suitable for infants of mothers who suffered from one or more of diabetes type I, diabetes type II, overweight and obesity during pregnancy. These metabolic disorders are a particular cause of reduced DHA and/or DHA precursor transmittal of the mother to the infant and may result in increased DPAn-6 incorporation into the brain membranes.

n-3 polyunsaturated fatty acid fraction:

Abbreviations for omega 3 (n-3) fatty acids: ALA=C18: 3n-3=alpha-linolenic acid; EPA=20:5n-3=eicosapentaenoic acid; DPAn-3=22:5n-3=n-3 docosapentaenoic acid; DHA=22:6n-3=docosahexaenoic acid.

The present composition contains a n-3 polyunsaturated fatty acid fraction comprising at least 0.1 wt %, preferably between 0.10 and 1 wt. %, more preferably between 0.15 and 0.5 wt. % DHA based on total weight of the lipid. The present composition contains at least 0.01 wt %, preferably between 0.015 and 0.5 wt % DPAn-3 based on total weight of the lipid. The EPA content is at least 0.01 wt. %, preferably between 0.03 and 0.5 wt. %, even more preferably between 0.04 and 0.1 wt. % based on total weight of the lipid.

The cumulative weight % (sum) of DHA, DPA and EPA in the present composition is below 1 wt. %, preferably below 0.5 wt. % of total lipid.

The present composition has a weight ratio EPA/DHA between 0.05 and 1, preferably between 0.1 and 0.5, more preferably between 0.2 and 0.5. The weight ratio DHA/DPAn-3 of the present composition is between 2 and 25, preferably between 5 and 15. The weight ratio (DPAn-3+EPA)/DHA of the present composition is between 0.25 and 1. More optimally, the weight ratio (precursors of DHA/DHA), i.e. (DPAn-3+EPA)/DHA, is between 0.3 and 0.5. In mothers milk, the weight ratio DPAn-3/EPA is generally greater than 1. The present composition preferably has a weight ratio DPAn-3/EPA between 0.25 and 5, more preferably between 0.3 and 3. Particular DPAn-3-enriched fish oils, selected seal oils and biotechnologically produced high DPAn-3 oils may suitably be used for making the composition according to the present invention.

The present composition contains between 1.9 and 3 wt. %, preferably between 2 and 2.5 wt. % ALA based on total weight of the lipid. The wt. % ALA is slightly increased compared to mother's milk. Mothers milk generally contains between about 0.5 and 1.6 wt. % ALA based on total weight of the lipid. However, mothers milk generally contains an increased weight percentage of long chain precursors of DHA, e.g. DPAn3 and EPA. Hence, the weight ratio ALA/DHA is higher in the present composition compared to mother's milk, i.e. between 5 and 25 in the present composition, versus about 2 in mother's milk. Preferably the ratio ALA/DHA in the present composition is between 7.5 and 15.

n-6 polyunsaturated fatty acid fraction:

Abbreviations for omega 6 (n-6) fatty acids: LA=18:2n-6=linoleic acid; GLA=18:3n-6=gamma-linolenic acid; DGLA=20:3n-6=dihomo-gamma-linolenic acid; AA=20:4n-6=arachidonic acid; DPAn-6=22:5n-6=n-6 docosapentaenoic acid.

The present composition contains between 0.2 and 1 wt. %, preferably between 0.25 and 0.75 wt. % AA based on total weight of the lipid. AA cannot be incorporated into the composition in to high amounts because of its pro-inflammatory effects. Hence, as a precursor of AA, the present composition preferably contains between 0.05 and 1 wt. %, preferably between 0.1 and 0.4 wt. %, more preferably between 0.15 and 0.3 wt. % GLA based on total weight of the lipid. The high content of GLA is included in the present composition to at least partially compensate for the reduced amount of DGLA in the present composition compared to human milk. As still the cumulative amount of precursor is relatively low, the present composition contains a high amount of LA, i.e. between 10 and 15 wt. %, preferably between 11 and 14 wt. % LA based on total weight of the lipid, which is slightly elevated compared to the average content of LA in human milk, which is about 9 wt. % (Luukainen at al, Eur J Pediatr (1995) 154: 316-319). The incorporation of the present amounts of GLA and the optimal n-3 polyunsaturated fatty acid fraction does however not require excessive amounts of LA to be included in the present composition, i.e. above 15 wt. % LA based on total lipid.

The weight ratio LA/ALA in the present composition is between 5 and 10.

Infant nutrition:

The present invention relates to nutritional formula suitable for feeding to an infant, i.e. nutritional compositions wherein the carbohydrate provides 40 to 75%, the lipid provides 20 to 50% and the protein provides 5 to 12.5% of the total calories. Preferably the protein provides 7.5 to 12.5% of the total calories.

The present composition contains at least one vegetable lipid source and a DPAn-3 containing lipid source. More preferably, the present composition contains at least one lipid source selected from the group consisting of evening primrose oil, borage oil and blackcurrant seed oil; at least one lipid source selected from the group consisting of canola oil, sunflower oil, coconut oil, palm oil and soybean oil; and at least one DPAn-3 containing lipid source, In a further preferred embodiment, the present composition also contains a fungal oil. Preferably the DPAn-3 containing lipid source contains at least 1 wt. %, even more preferably at least 2 wt. % DPA n-3 based on fatty acids of the DPAn-3 containing lipid source. For easy manufacturing, the DPAn-3 containing lipid source contains at least 15 wt. %, more preferably at least 20 wt. % DHA, even more preferably at least 25 wt. % DHA based on fatty acids of the DPAn-3 containing lipid source.

In a further aspect the present invention provides a method for treating infants of a mother who suffered from a metabolic disorder during pregnancy by administering the present composition.

For the preparation of the present composition, a blend of animal and vegetable lipid sources is used. Because the fatty acid constitution of lipid sources can vary significantly (even if obtained from the same plant or animal source), it is best to first analyze the lipid source to be used and than calculate the amounts of individual oils that are needed to achieve the present composition and admix the lipid sources. Alternatively, the skilled person can find the appropriated lipid sources in proper handbooks. The lipid source used are preferably of non-human origin. The fatty acids as described in the present invention may be provided as free fatty acids, in triglyceride form, in phospholipid form, or as a mixture of one of more of the above.

The carbohydrate of the present composition is preferably provided mainly by lactose, because it is most suitable for feeding the infant. Hence, the digestible carbohydrate fraction (carbohydrate) preferably contains at least 50 wt. %, more preferably at least 90 wt. % lactose based on total weight of the carbohydrate fraction.

Sleep is also of utmost importance for proper intellectual development of the infant. Hence, the infant preferably has reduced intestinal discomfort. Water-soluble indigestible fibers contribute a reduced occurrence of intestinal discomfort such as bloating. Hence, the present composition preferably also contains between 0.2 and 5 grams water-soluble indigestible fiber per 100 kcal of the present composition, more preferably between 0.5 and 1.5 gram per 100 kcal. Preferably the present composition contains at least one water-soluble indigestible fiber selected from the group consisting of galactooligosaccharide, fructooligosaccharide and inulin.

Optimal brain development is of particular importance for the baby the first few months of life. Hence, the present invention particularly relates to nutritional formulas, which are optimally suitable for feeding during the first few months of life. A caloric content of between 0.600 and 0.800 kcal per ml is believed to reduce intestinal discomfort in these young infants and thereby stimulate the uptake of fatty acids. Hence, the present composition preferably contains between 0.600-0.800 kcal/ml, more preferably 0.650-0.680 kcal/ml.

As the infants of mothers who suffered from a disease during pregnancy may have sometimes have to catch-up on neurological tissue development, the present invention preferably comprises nucleotides. The present composition preferably also comprises between 2 and 25 mg nucleotides and/ or between 2 and 25 mg nucleosides per 100 kcal, more preferably between 3 and 10 mg nucleotides per 100 kcal. The present composition preferably contains at least 2 nucleotides selected from the group consisting of cytidine-5-monophosphate, uridine-5-monophosphate, adenosine-5-monophosphate, guanosine-5-monophosphate and inosine-5-monophosphate. The nucleotides and/or nucleosides further stimulate the immune system, acting synergistically with the other ingredients of the present composition.

EXAMPLES

Example 1

Infant Formula

A liquid infant nutrition, prepared by admixing 13.9 g powder with water to yield 100 ml final product, said liquid product comprising per 100 ml:
Energy: 66 kcal
Protein: 8 en %
Digestible Carbohydrates: 44 en % (containing 7.3 g lactose)
Lipid: 48 en % (containing, based on total weight of the lipid 0.2 wt. %
DHA; 0.02 wt. % DPAn-3; 0.05 wt. % EPA; 2.2 wt. % ALA, 0.2 wt. % GLA; 0.35 wt. % AA, 13 wt. % LA)
Fibre: 0.8 g (containing 0.05 g fructopolysaccharide (Raftiline HP™, Orafti, Tienen, Belgium); 0.55 g transgalactooligosaccharides (Vivinal-GOS™ (Borculo Demo Ingredients, Netherlands); 0.20 g pectin hydrolysate prepared as described in EP1373543, example 1.
Nucleotides: 0.89 mg Cytidine-5-monophosphate;
0.55 mg Uridine-5-monophosphate;
0.82 mg Adenosine-5-monophosphate;
0.20 mg Guanosine-5-monophosphate;
0.34 mg Inosine-5-monophosphate.
Osmolarity: 300 mOsmol/l
The composition further contains choline (6 mg/100 ml) and taurine (6.3 mg/100 ml); minerals and trace elements (including 2 mg zinc/100 ml) and vitamins in amounts in compliance with the international guidelines for infant milk formula.

The invention claimed is:

1. A method for treating infants of a mother who suffered from diabetes type I, diabetes type II, obesity or overweight during pregnancy, said method comprising feeding a liquid nutritional composition to said infant, wherein:
said liquid nutritional composition comprises a lipid; and
said lipid comprises an n-3 polyunsaturated fatty acid fraction which comprises:
(a) at least 0.1 wt. % docosahexaenoic acid (DHA) based on total weight of the lipid;
(b) at least 0.01 wt. % n-3 docosapentaenoic acid (DPAn-3) based on total weight of the lipid; and
(c) at least 0.01 wt. % eicosapentaenoic acid (EPA) based on total weight of the lipid; and wherein the sum of DHA, DPAn-3 and EPA is below 1 wt. % of total lipid.

2. The method of claim 1, wherein said lipid further comprises an n-6 polyunsaturated fatty acid fraction which comprises:
(a) between 0.05 and 0.4 wt. % gamma linoleic acid (GLA) based on total weight of the lipid;
(b) between 0.2 and 1 wt. % arachidonic acid (AA) based on total weight of the lipid; and
(e) between 10 and 15 wt. % linoleic acid (LA) based on total weight of the lipid.

3. The method of claim 1, wherein said n-3 polyunsaturated fatty acid fraction further comprises between 1.5 and 3 wt. % alpha linoleic acid (ALA) based on total weight of the lipid.

4. The method of claim 2, wherein said n-3 polyunsaturated fatty acid fraction further comprises between 1.5 and 3 wt. % alpha linoleic acid (ALA) based on total weight of the lipid.

5. The method of claim 4, wherein the weight ratio of LA/ALA is between 5 and 10.

6. The method of any one of claims 1-5, wherein:
   the weight ratio of EPA/DHA is between 0.05 and 1;
   the weight ratio of (DPAn-3 EPA)/DHA is between 0.25 and 1;
   the weight ratio of DPAn-3/EPA is between 0.25 and 5; and
   the weight ratio of DHA/DPAn-3 is between 2 and 25.

* * * * *